(12) United States Patent
Yoo (10) Patent No.: US 7,926,143 B2
(45) Date of Patent: Apr. 19, 2011

(54) VACUUM CLEANER

(75) Inventor: Dong-hun Yoo, Gwangju (KR)

(73) Assignee: Samsung Gwangju Electronics Co., Ltd., Gwangju (KR)

( * ) Notice: Subject to any disclaimer, the term of this patent is extended or adjusted under 35 U.S.C. 154(b) by 350 days.

(21) Appl. No.: 12/150,642

(22) Filed: Apr. 30, 2008

(65) Prior Publication Data
US 2009/0119869 A1    May 14, 2009

(30) Foreign Application Priority Data

Nov. 13, 2007 (KR) ................. 10-2007-0115248

(51) Int. Cl.
*A47L 5/00* (2006.01)
(52) U.S. Cl. ............... 15/339; 15/319; 15/354
(58) Field of Classification Search .......... 15/339, 15/319, 307, 354–361
See application file for complete search history.

(56) References Cited

U.S. PATENT DOCUMENTS

| | | | | |
|---|---|---|---|---|
| 4,905,343 | A * | 3/1990 | Jailor ............... | 15/328 |
| 5,968,455 | A * | 10/1999 | Brickley ........... | 422/121 |
| 6,782,584 | B2 * | 8/2004 | Choi ................. | 15/352 |
| 7,313,845 | B2 * | 1/2008 | Nam .................. | 15/339 |
| 7,610,652 | B2 * | 11/2009 | Seo et al. .......... | 15/347 |
| 2003/0221279 | A1 | 12/2003 | Oh et al. ........... | 15/353 |

FOREIGN PATENT DOCUMENTS

| | | |
|---|---|---|
| EP | 1695648 | 8/2006 |
| GB | 2389036 | 12/2003 |
| KR | 100232536 | 9/1999 |
| KR | 100603209 | 7/2006 |

OTHER PUBLICATIONS

British Combined Search and Examination Report dated Dec. 12, 2008 corresponding to Application No. GB0814723.3.

* cited by examiner

*Primary Examiner* — Dung Van Nguyen
(74) *Attorney, Agent, or Firm* — Ohlandt, Greeley, Ruggiero & Perle, LLP (57) ABSTRACT

A vacuum cleaner is provided which includes a cleaner body in which a ultraviolet (UV) irradiation unit is mounted in a dust receptacle mounting unit, a dust receptacle detachably mounted in the dust receptacle mounting unit, the dust receptacle comprising a UV transmission window formed in a position facing the UV irradiation unit, and a switching device mounted in the dust receptacle mounting unit to switch power applied to the UV irradiation unit according to whether the dust receptacle is mounted. Accordingly, power is applied to a UV lamp only when the dust receptacle is mounted in the vacuum cleaner, so there is no risk that a user is exposed to UV rays emitted from the UV lamp when the user separates the dust receptacle from the vacuum cleaner.

8 Claims, 7 Drawing Sheets

VACUUM CLEANER

CROSS-REFERENCE TO RELATED APPLICATIONS

This application claims the benefit under 35 U.S.C. §119 from Korean Patent Application No. 10-2007-0115248, filed on Nov. 13, 2007, in the Korean Intellectual Property Office, the disclosure of which is incorporated herein by reference in its entirety.

BACKGROUND OF THE INVENTION

1. Field of the Invention

The present disclosure relates to a vacuum cleaner, and more particularly, to a vacuum cleaner that has an ultraviolet (UV) sterilizing lamp to disinfect a dust receptacle for collecting impurities.

2. Description of the Related Art

Vacuum cleaners generally collect dust on surfaces being cleaned by drawing in ambient air, using negative pressure generated by a vacuum source mounted in a cleaner body. With the recent boom in interest in healthy life-styles, vacuum cleaners having an ultraviolet (UV) sterilizing lamp provided on the cleaner body have been introduced in order to remove germs that may exist in dust collected in a dust receptacle in the cleaner as well as collecting the dust.

Korean Patent Registration No. 10-0232536 discloses a vacuum cleaner having a UV sterilizing lamp for killing worms or ticks in a dust bag, and a transparent quartz glass board is mounted on the front of the UV sterilizing lamp mounting portion to protect the UV sterilizing lamp from foreign substances.

However, a UV sterilizing lamp of a conventional vacuum cleaner configured as described above is operated only when the vacuum cleaner is used, so the sterilizing time is restricted by the operating time of the vacuum cleaner. Accordingly, the efficiency of the UV sterilizing lamp in sterilizing collected dust is low.

SUMMARY OF THE INVENTION

Exemplary embodiments of the present disclosure overcome the above and other disadvantages. Also, the present disclosure is not required to overcome the disadvantages described above, and an exemplary embodiment of the present disclosure may not overcome any of the problems described above.

The present disclosure provides an improved vacuum cleaner capable of performing an ultraviolet (UV) sterilization function when power is supplied to the vacuum cleaner, regardless of whether the vacuum cleaner is being operated.

The present disclosure also provides a vacuum cleaner having an improved structure in which power is applied to or removed from a UV lamp according to whether a dust receptacle is mounted, so that a user may safely use the vacuum cleaner.

The above aspects and/or other features of the present disclosure can substantially be achieved by providing a vacuum cleaner that includes a cleaner body in which an ultraviolet (UV) irradiation unit is mounted in a dust receptacle mounting unit, a dust receptacle detachably mounted in the dust receptacle mounting unit, the dust receptacle comprising a UV transmission window formed in a position facing the UV irradiation unit, and a switching device mounted in the dust receptacle mounting unit to switch power applied to the UV irradiation unit according to whether the dust receptacle is mounted.

The switching device may include a switching member protruding from the dust receptacle mounting unit in a position facing the dust receptacle, and a switching projection protruding from the dust receptacle in a position facing the switching member, to apply pressure to the switching member in a mounting position of the dust receptacle.

A guide rib may extend from a circumference of the switching member to guide movement of the switching projection.

The UV transmission window may be configured with an opening disposed in a position facing the UV irradiation unit of the dust receptacle mounting unit, and with a fluoropolymer or Teflon film attached to the opening.

The UV irradiation unit may include a UV lamp, and a protection grill in which to house the UV lamp.

The above aspects and other features of the present disclosure can substantially be achieved by providing a vacuum cleaner that includes a cleaner body in which an ultraviolet (UV) irradiation unit is mounted in a dust receptacle mounting unit, a dust receptacle detachably mounted in the dust receptacle mounting unit, the dust receptacle comprising a UV transmission window formed in a position facing the UV irradiation unit, a lifting unit to move the dust receptacle upwards or downwards, and a switching device mounted in the dust receptacle mounting unit to switch power applied to the UV irradiation unit according to vertical movement of the dust receptacle.

The lifting unit may include an adjustment lever to rotate to adjust the extent of a mounting position of the dust receptacle, and a lifting board to move the dust receptacle upwards or downwards according to a change in the mounting position of the dust receptacle adjusted by the adjustment lever.

The switching device may include a switching member protruding from the dust receptacle mounting unit in a position facing the dust receptacle, and a switching projection protruding from the dust receptacle in a position facing the switching member, to apply pressure to the switching member in the mounting position of the dust receptacle.

A guide rib may extend from a circumference of the switching member to guide the ascent and descent of the switching projection. The guide rib may restrict further ascent of the switching projection when the dust receptacle reaches the highest point.

The UV transmission window may be configured with an opening disposed in a position facing the UV irradiation unit of the dust receptacle mounting unit, and with a fluoropolymer or Teflon film attached to the opening.

The UV irradiation unit may include a UV lamp, and a protection grill in which to house the UV lamp.

As described above, according to the present disclosure, if a power cord included in the vacuum cleaner is inserted into a power outlet and if power is supplied to the vacuum cleaner, the inside of the dust receptacle may be disinfected using UV rays, regardless of whether the vacuum cleaner is being operated. Accordingly, it is possible to sterilize dust collected in the cleaner effectively and completely.

Additionally, power is applied to a UV lamp only when the dust receptacle is mounted in the vacuum cleaner, so there is no risk that a user is exposed to UV rays emitted from the UV lamp even if the user separates the dust receptacle from the vacuum cleaner when the power cord is being connected to the power outlet.

Other objects, advantages and salient features of the disclosure will become apparent from the following detailed description and drawings.

BRIEF DESCRIPTION OF THE DRAWINGS

These and/or other aspects and advantages of the disclosure will become apparent and more readily appreciated from the following description of the embodiments, and accompanying drawings in which.

Throughout the drawings, like reference numerals will be understood to refer to like parts, components and structures.

DETAILED DESCRIPTION OF EXEMPLARY EMBODIMENTS

Hereinafter, a vacuum cleaner will be described in detail with reference to the accompanying drawings.

Referring to FIGS. 1 to 4, an upright-type vacuum cleaner includes a cleaner body 10, a dust receptacle 20 and a switching device 30.

Figure 1:
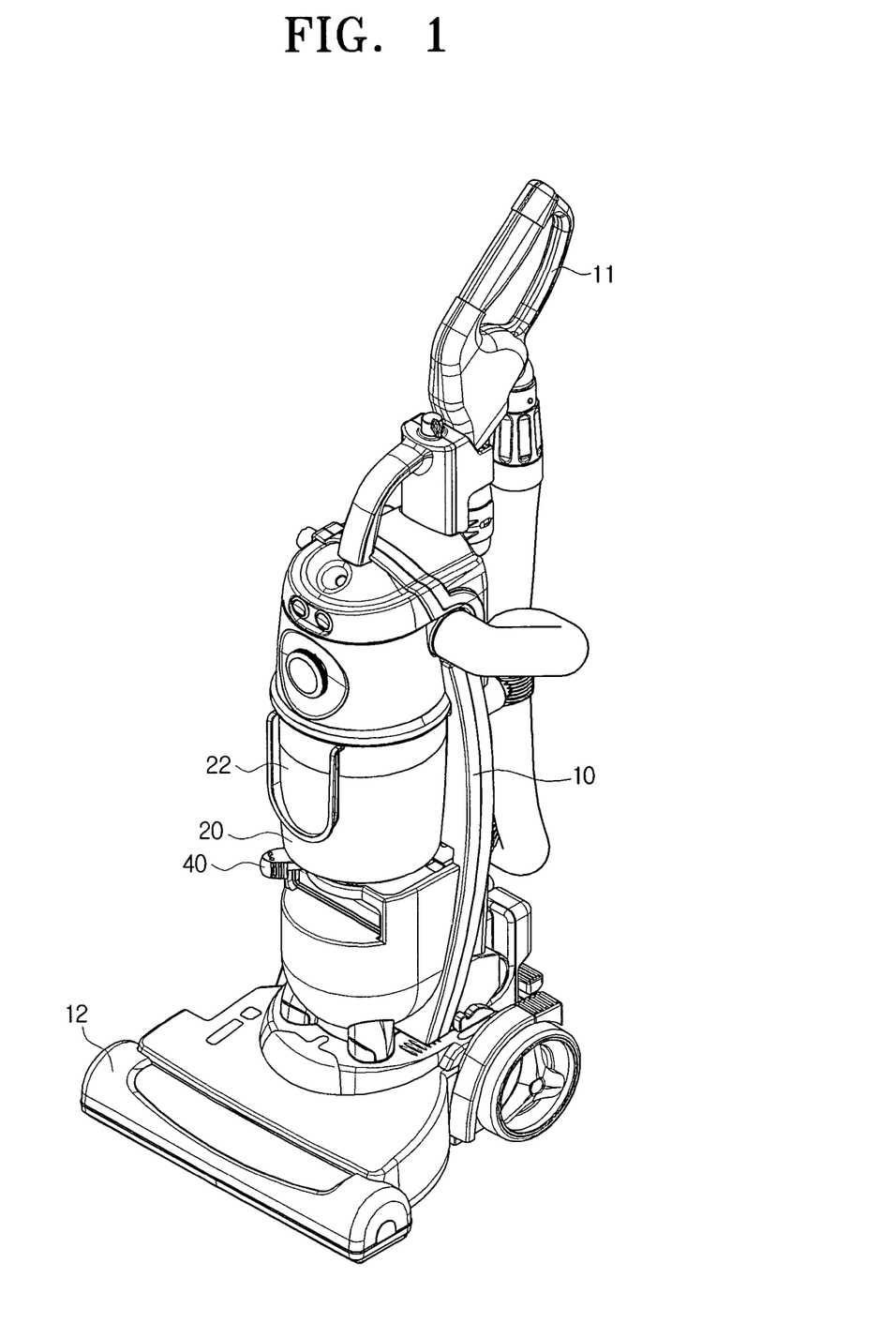
FIG. 1 is a view of a vacuum cleaner.
Figure 2:
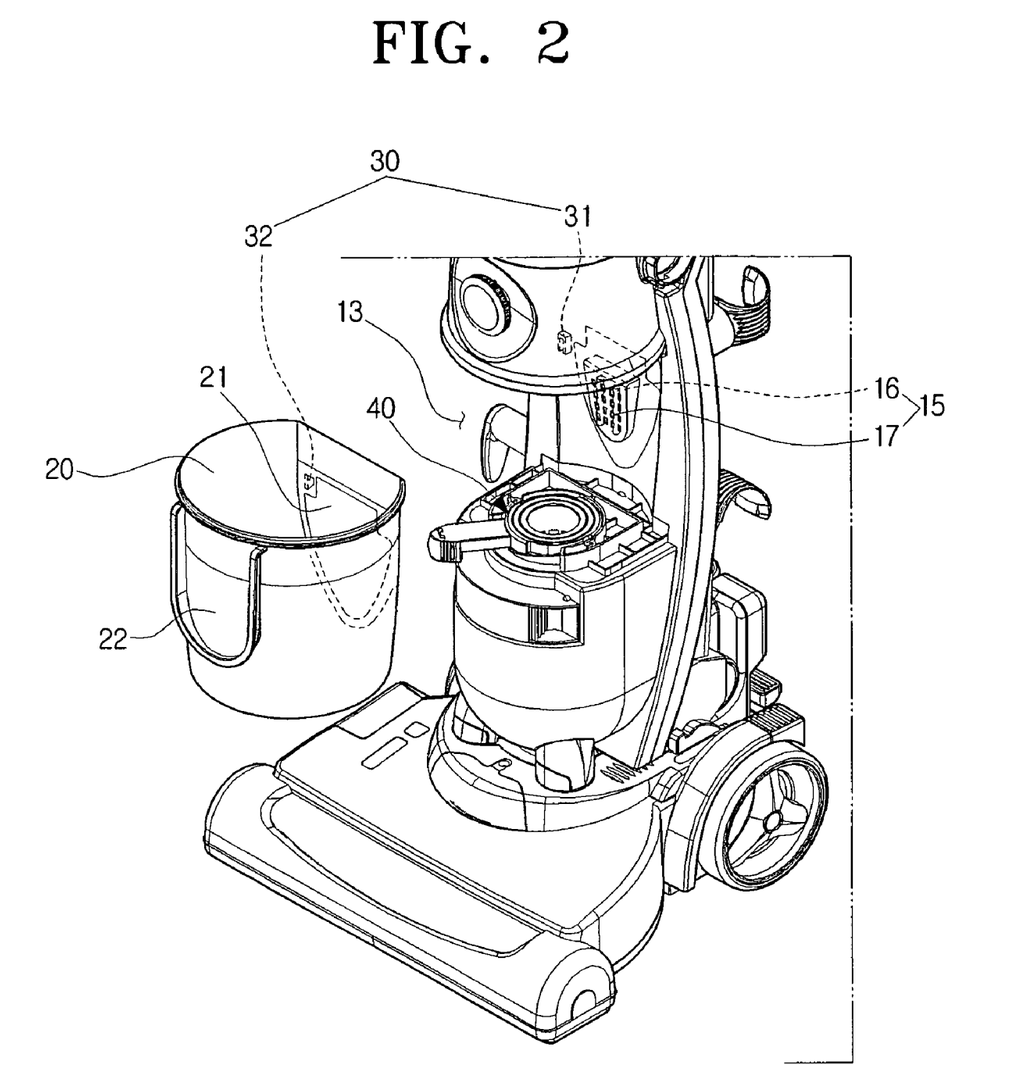
FIG. 2 is a close-up view of the vacuum cleaner of FIG. 1 from which a dust receptacle has been separated.

The cleaner body 10 includes a grip unit 11 whereby a user can grip the vacuum cleaner, and a suction brush 12 to draw in dust-laden air. As shown in FIG. 2, a dust receptacle mounting unit 13 is provided in which a dust receptacle 20 is detachably mounted. The dust receptacle mounting unit 13 includes an ultraviolet (UV) irradiation unit 15 disposed in a position facing the dust receptacle 20.

The UV irradiation unit 15 includes a UV lamp 16 and a protection grill 17.

When a power cord (not shown) included in the cleaner body 10 is inserted into a power outlet, and when power is supplied to the cleaner body 10, the UV lamp 16 may be illuminated even if the vacuum cleaner is not operated. Additionally, the switching device 30 may cause power to be selectively applied to the UV lamp 16 so that the UV lamp 16 may be illuminated only when the dust receptacle 20 is mounted in a correct position in the dust receptacle mounting unit 13.

Figure 3:
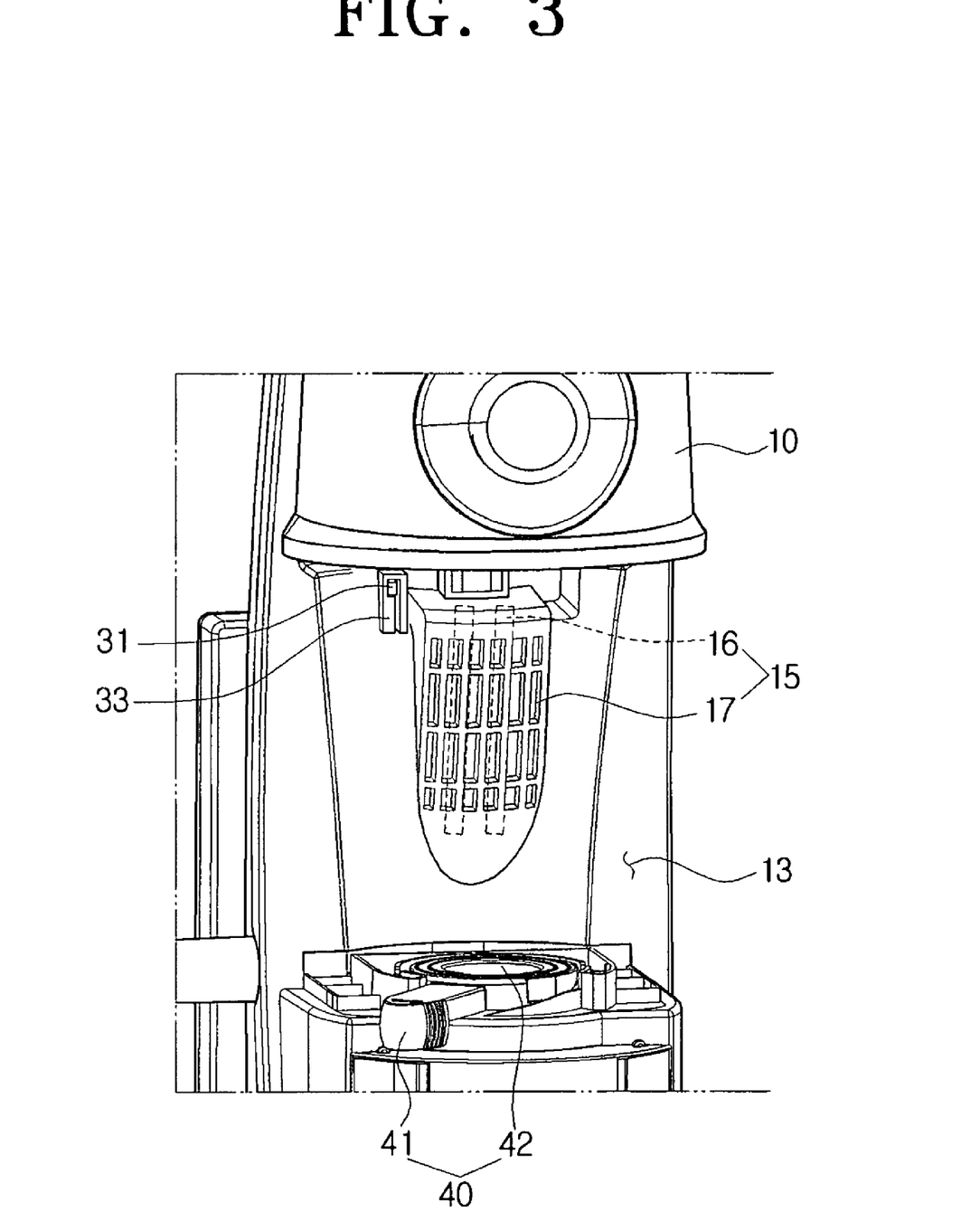
FIG. 3 is a perspective view showing a switching member and a UV irradiation unit provided in a dust receptacle mounting unit in a cleaner body.

The protection grill 17 may protect the UV lamp 16 from external shock. In order to achieve this, the UV lamp 16 may be mounted in a space formed in the protection grill 17. As shown in FIG. 3, the protection grill 17 includes a plurality of slots arranged lengthwise along the UV lamp 16 to permit UV transmission therethrough.

Figure 4:
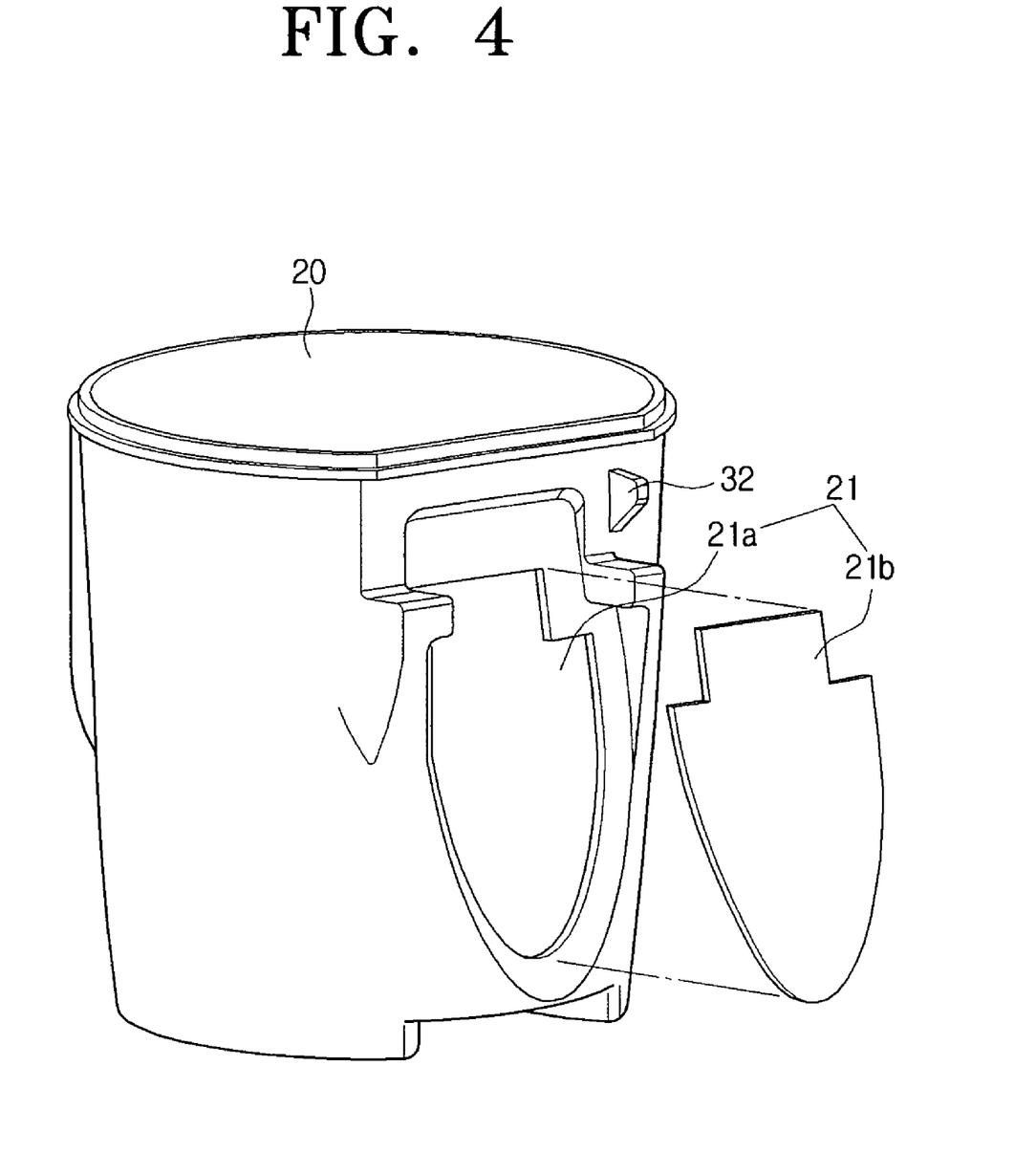
FIG. 4 is a perspective view showing a dust receptacle including a switching projection and a UV transmission window cleaner.

Referring to FIGS. 2 and 4, the dust receptacle 20 is detachably mounted in the dust receptacle mounting unit 13. A UV transmission window 21 is disposed on the dust receptacle 20 in order to transmit UV rays emitted from the UV irradiation unit 15 to the inside of the dust receptacle 20. The UV transmission window 21 is configured with an opening 21a and a fluoropolymer or Teflon film 21b. Here, the opening 21a may desirably be disposed in a position facing the UV irradiation unit 15, and the fluoropolymer or Teflon film 21b having superior UV transmittance may desirably be attached to the opening 21a so as to cover the opening 21a. The UV transmission window 21 may have a hollowed-out shape corresponding to the UV irradiation unit 15. Accordingly, when the dust receptacle 20 is mounted in the cleaner body 10, interference between the UV transmission window 21 and UV irradiation unit 15 may be reduced and the volume of the vacuum cleaner may be minimized. Additionally, the dust receptacle 20 may further include a transparent observation window 22 through which a user can observe the inside of the dust receptacle 20 with the unaided eye to check the amount of dust collected therein. Alternatively, the dust receptacle 20 may be made of transparent material.

The switching device 30 may detect whether the dust receptacle 20 is disposed in a correct mounting position of the cleaner body 10, and may cause power to be applied to or removed from the UV irradiation unit 15 according to a result of the detecting operation. The switching device 30 includes a switching member 31 and a switching projection 32.

As shown in FIG. 3, the switching member 31 is disposed so as to face the dust receptacle 20 mounted in the dust receptacle mounting unit 13. Additionally, a guide rib 33 is disposed adjacent to the switching member 31 to guide the switching projection 32 into place. The switching member 31 may be a generally used micro-switch, so if pressure is applied, the micro-switch may be on, and if pressure is released, the micro-switch may be off.

The switching projection 32 of the dust receptacle 20 may desirably be disposed in a position facing the switching member 31, as shown in FIGS. 2 and 4. The switching projection 32 may be injection molded with the dust receptacle 20, or an extra member may be attached to or combined with the dust receptacle 20 to function as a switching projection 32.

A vacuum cleaner may further include a lifting unit 40. In this situation, the switching device 30 may cause power to be selectively applied to or removed from the UV irradiation unit 15 in engagement with the movement of the dust receptacle 20, which is capable of being moved up or down by the lifting unit 40.

Figure 5:
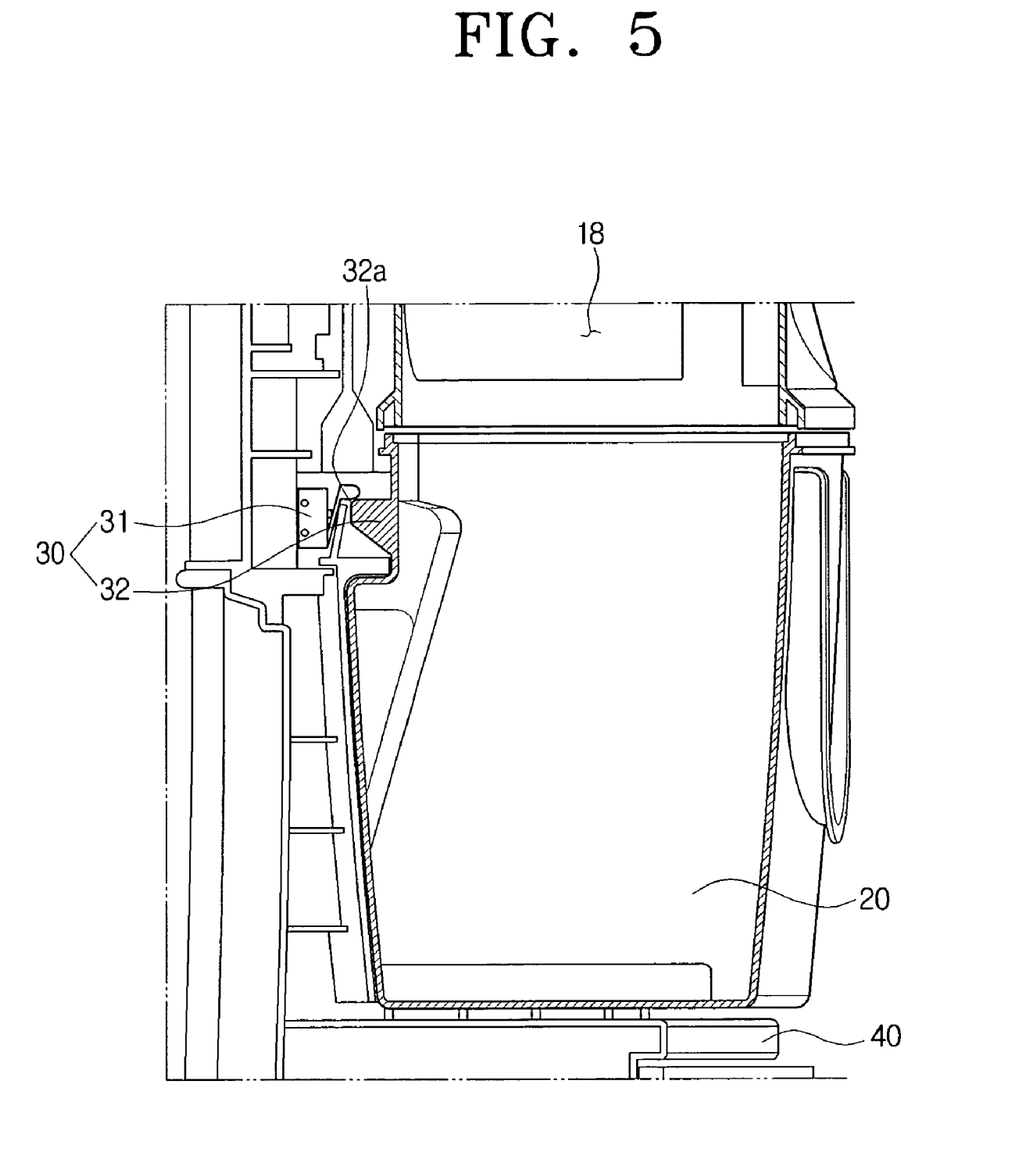
FIG. 5 is a cross-sectional view of the dust receptacle of the vacuum cleaner of FIG. 1 when the dust receptacle is moved down by a lifting unit.
Figure 6:
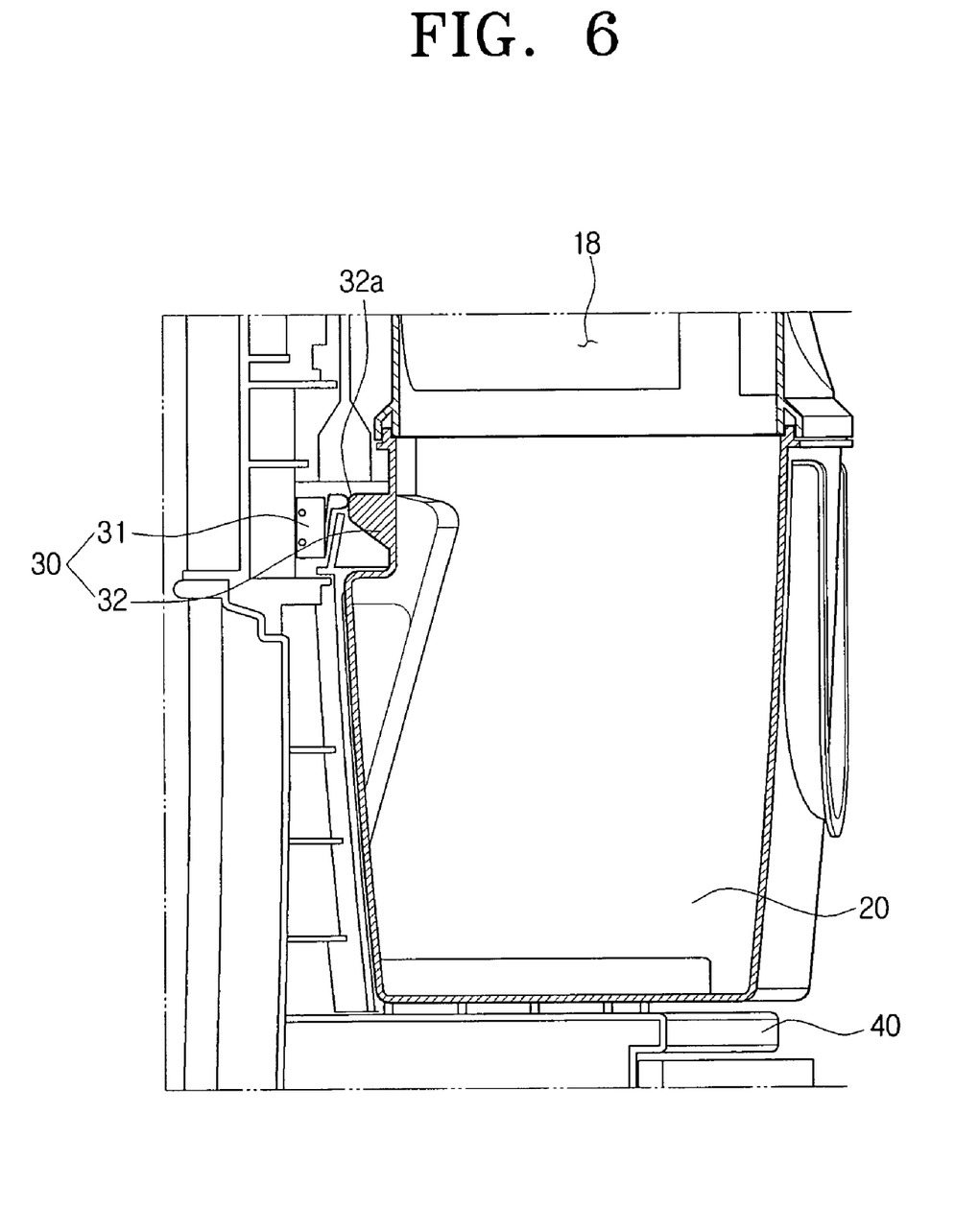
FIG. 6 is a cross-sectional view of the dust receptacle of the vacuum cleaner of FIG. 1 when the dust receptacle is moved up by a lifting unit.
Figure 7:
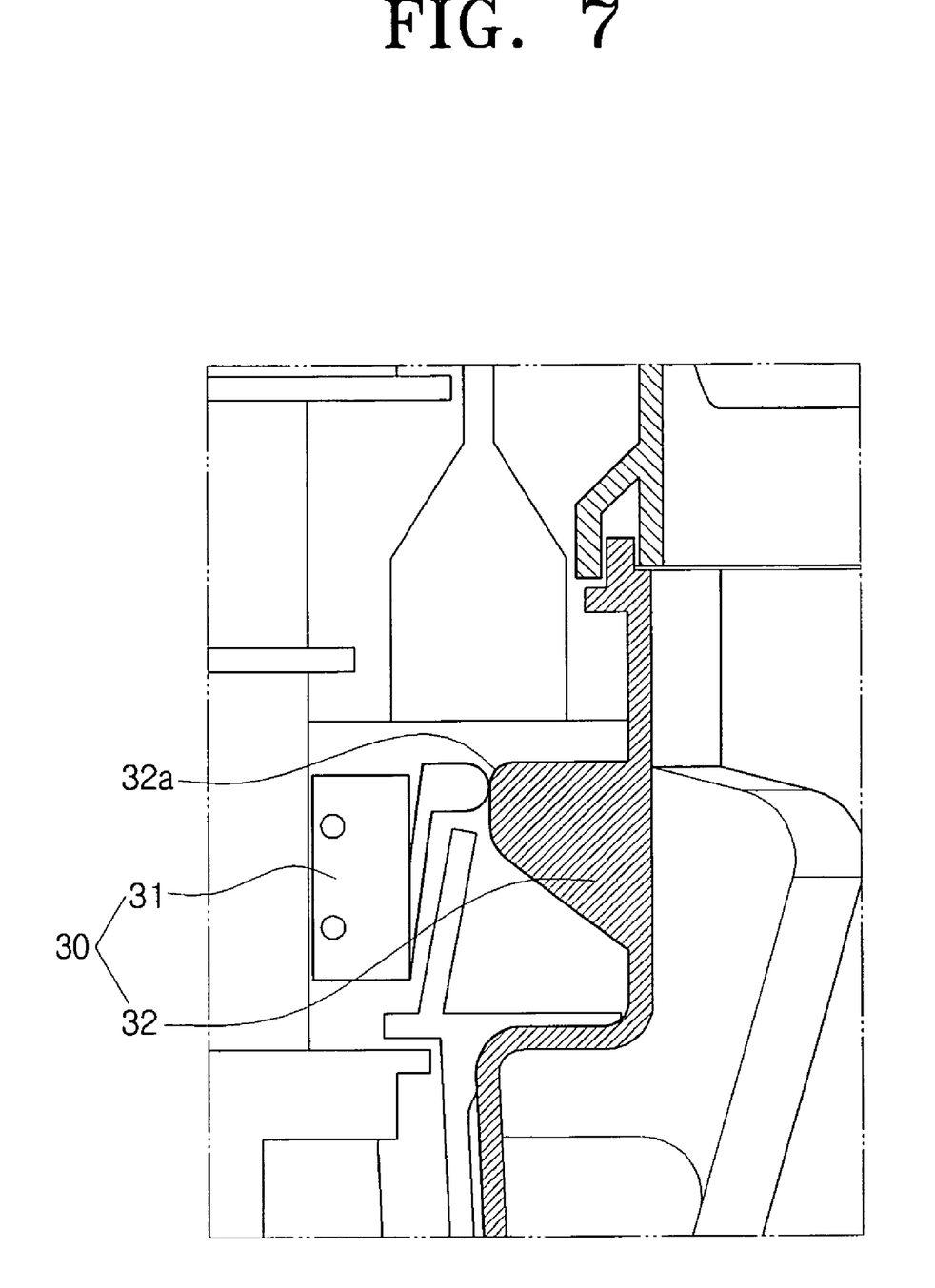
FIG. 7 is an enlarged, sectional view of a switching device shown in FIG. 6.

Since the configurations of the cleaner body 10, dust receptacle 20 and switching device 30 are the same as those described above, detailed description thereof will be omitted. In this situation, the switching projection 32 may be in contact with or spaced apart from the switching member 31 according to the vertical sliding operation of the dust receptacle 20. As shown in FIGS. 5 to 7, an edge 32a of the switching projection 32 which is in contact with the switching member 31 is rounded, so the switching operation of the switching member 31 can be performed smoothly. Additionally, the guide rib 33 may desirably be formed so that an upper portion thereof may be blocked to restrict the vertical sliding operation of the switching projection 32 of the dust receptacle 20, as shown in FIG. 3.

The lifting unit 40 may desirably include an adjustment lever 41 and a lifting board 42, as shown in FIG. 3. The adjustment lever 41 may rotate to adjust the elevation of the lifting board 42, so that the height at which the dust receptacle 20 is mounted may be regulated. The present disclosure is applicable to a lifting unit including a lifting board, the elevation of which may be adjusted according to the rotation of an adjustment lever 41.

Hereinafter, operations of the vacuum cleaner of the present disclosure will be described.

In order to use the vacuum cleaner, the user connects a power cord (not shown) to a power outlet on a wall or the like, so power may be supplied to the cleaner body 10. When power is supplied to the cleaner body 10, UV rays may be emitted from the UV irradiation unit 15 in the cleaner body 10, regardless of whether a vacuum source, such as a suction motor, (not shown) of the cleaner is being driven, so that the inside of the dust receptacle 20 can be disinfected. In order to achieve this, the opening 21a of the dust receptacle 20 faces the UV irradiation unit 15, and the fluoropolymer or Teflon film 21b is attached to cover the opening 21a so that the UV transmission window 21 may be formed. Accordingly, the UV rays emitted by the UV irradiation unit 15 in the cleaner body 10 can be easily transmitted to the inside of the dust receptacle 20 through the UV transmission window 21.

If the user starts the cleaning operation using the vacuum cleaner, dust-laden air may be drawn in from the suction brush 12 using negative pressure generated by a suction motor (not shown) driven by the applied power, and dust may be collected in the dust receptacle 20 through a filtering process. The dust collected in the dust receptacle 20 may then be sterilized using the UV rays projected by the UV irradiation unit 15.

If the dust receptacle 20 is full of dust, the user may detach the dust receptacle 20 from the vacuum cleaner and empty the dust receptacle 20. In this situation, if the user separates the power cord of the vacuum cleaner from the power outlet and detaches the dust receptacle 20 from the vacuum cleaner, the operation of the UV irradiation unit 15 may be stopped, so the risk of UV exposure may be removed. However, since the user may not always detach the dust receptacle 20 from the vacuum cleaner after separating the power cord from the power outlet, the switching device 30 may be needed to prevent UV exposure.

The switching device 30 may cause power to be selectively applied to the UV irradiation unit 15 according to whether the dust receptacle 20 is mounted. In more detail, if the dust receptacle 20 is attached to the cleaner body 10, the switching projection 32 protruding from the dust receptacle 20 may apply pressure to the switching member 31 of the dust receptacle mounting unit 13 to close a circuit so that power may be supplied to the UV irradiation unit 15. Alternatively, if the dust receptacle 20 is detached from the cleaner body 10, the switching projection 32 protruding from the dust receptacle 20 may be spaced apart from the switching member 31 of the dust receptacle mounting unit 13 so that the switching member 31 may open the circuit. Accordingly, the power supply to the UV irradiation unit 15 may be suspended.

Therefore, if the dust receptacle 20 is separated from the cleaner body 10 even when the vacuum cleaner is turned on, power supplied to the UV irradiation unit 15 may be cut off by the switching device 30, so there is no risk of the user being exposed to UV rays from the UV irradiation unit 15.

The vacuum cleaner according to the second exemplary embodiment of the present disclosure may further include the lifting unit 40 to enable the dust receptacle 20 to be attached to or detached from the cleaner body 10 more easily.

In this situation, in order to attach the dust receptacle 20 to the vacuum cleaner, the user may slide the dust receptacle 20 upwards into the dust receptacle mounting unit 13 so that the dust receptacle 20 may be sealed in contact with a dust collecting unit 18 (see FIG. 5). In order to detach the dust receptacle 20 from the vacuum cleaner, the user may slide the dust receptacle 20 downwards from the dust receptacle mounting unit 13 so that the dust receptacle 20 and the dust collecting unit 18 may be disconnected.

FIGS. 5 to 7 show the operations of the switching device 30 according to the movement of the lifting unit 40.

As shown in FIG. 5, the dust receptacle 20 is inserted into the dust receptacle mounting unit 13 when the lifting unit 40 moves down to its lowest point. In this situation, no interference arises between an upper portion of the dust receptacle 20 and the dust collecting unit 18, so the user can insert the dust receptacle 20 into the dust receptacle mounting unit 13 without further effort.

Additionally, since the switching projection 32 is spaced apart from the switching member 31, the switching member 31 causes the circuit to be open so that the power supply to the UV irradiation unit 15 is cut off.

If the dust receptacle 20 is completely inserted into the dust receptacle mounting unit 13, the user may operate the lifting unit 40 to move the dust receptacle 20 upwards so that the dust receptacle 20 may be firmly in contact with the dust collecting unit 18, as shown in FIG. 6.

In this situation, the switching projection 32 may apply pressure to the switching member 31 while moving upwards according to the ascent of the dust receptacle 20. The edge 32a of the switching projection 32 is rounded, so the switching projection 32 may be in smooth contact with the switching member 31. Additionally, the guide rib 33 is disposed adjacent to the switching member 31 to guide the movement of the switching projection 32, as shown in FIG. 3. Accordingly, even if the user inserts the dust receptacle 20 into the dust receptacle mounting unit 13 in a position deviating from the correct position, the guide rib 33 may guide the ascent and descent of the switching projection 32, so that the dust receptacle 20 may be mounted correctly.

As described above, the switching member 31 may close the circuit so that power may be applied to the UV irradiation unit 15, according to the pressure applying operation of the switching projection 32. Accordingly, power may be applied to the UV irradiation unit 15 only when the dust receptacle 20 is mounted in the correct mounting position even if the power cord of the vacuum cleaner is connected to the power outlet, so that UV rays from the UV irradiation unit 15 may be projected inside the dust receptacle 20, thereby ensuring safety against the risk of UV exposure.

The foregoing exemplary embodiments and advantages are merely exemplary and are not to be construed as limiting the present disclosure. The present teaching can be readily applied to other types of apparatuses. Also, the description of the exemplary embodiments of the present disclosure is intended to be illustrative, and not to limit the scope of the claims, and many alternatives, modifications, and variations will be apparent to those skilled in the art.

What is claimed is:

1. A vacuum cleaner, comprising:
   a cleaner body in which a ultraviolet (UV) irradiation unit is mounted in a dust receptacle mounting unit;
   a dust receptacle detachably mounted in the dust receptacle mounting unit, the dust receptacle comprising a UV transmission window formed in a position facing the UV irradiation unit; and
   a switching device mounted in the dust receptacle mounting unit to switch power applied to the UV irradiation unit according to whether the dust receptacle is mounted, wherein the switching device comprises:
   a switching member protruding from the dust receptacle mounting unit in a position facing the dust receptacle;
   a switching projection protruding from the dust receptacle in a position facing the switching member, so that pressure is applied to the switching member when the dust receptacle is in a mounting position; and a guide rib extending from a circumference of the switching member to guide movement of the switching projection.

2. The vacuum cleaner as claimed in claim 1, wherein the UV transmission window is configured with an opening disposed in a position facing the UV irradiation unit of the dust receptacle mounting unit, and with a fluoropolymer film attached to the opening.

3. The vacuum cleaner as claimed in claim 1, wherein the UV irradiation unit comprises:
  a UV lamp; and
  a protection grill configured to house the UV lamp.

4. A vacuum cleaner comprising:
  a cleaner body in which a ultraviolet (UV) irradiation unit is mounted in a dust receptacle mounting unit;
  a dust receptacle detachably mounted in the dust receptacle mounting unit, the dust receptacle comprising a UV transmission window formed in a position facing the UV irradiation unit;
  a lifting unit to move the dust receptacle upwards or downwards; and
  a switching device mounted in the dust receptacle mounting unit to switch power applied to the UV irradiation unit according to vertical movement of the dust receptacle, wherein the switching device comprises:
  a switching member protruding from the dust receptacle mounting unit in a position facing the dust receptacle;
  a switching projection protruding from the dust receptacle in a position facing the switching member so that pressure is applied to the switching member when the dust receptacle is in the mounting position; and
  a guide rib extending from a circumference of the switching member to guide the ascent and descent of the switching projection.

5. The vacuum cleaner as claimed in claim 4, wherein the lifting unit comprises:
  an adjustment lever to rotate to adjust the extent of a mounting position of the dust receptacle; and
  a lifting board to move the dust receptacle upwards or downwards according to a change in the mounting position of the dust receptacle adjusted by the adjustment lever.

6. The vacuum cleaner as claimed in claim 4, wherein the guide rib restricts further ascent of the switching projection when the dust receptacle reaches the highest point.

7. The vacuum cleaner as claimed in claim 4, wherein the UV transmission window is configured with an opening disposed in a position facing the UV irradiation unit of the dust receptacle mounting unit, and with a fluoropolymer film attached to the opening.

8. The vacuum cleaner as claimed in claim 4, wherein the UV irradiation unit comprises:
  a UV lamp; and
  a protection grill wherein to house the UV lamp.

* * * * *